US010551349B2

(12) United States Patent
Iannucci et al.

(10) Patent No.: US 10,551,349 B2
(45) Date of Patent: Feb. 4, 2020

(54) METHOD FOR DETERMINING DEFECT DEPTH IN FERROMAGNETIC STRUCTURES BASED ON MAGNETIC FLUX LEAKAGE DIRECTION

(71) Applicant: The Charles Stark Draper Laboratory, Inc., Cambridge, MA (US)

(72) Inventors: Michael J. Iannucci, Wellesley, MA (US); William J. Trinkle, Arlington, MA (US); Arturo D. Gossage, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 164 days.

(21) Appl. No.: 15/671,791

(22) Filed: Aug. 8, 2017

(65) Prior Publication Data
US 2018/0038833 A1    Feb. 8, 2018

Related U.S. Application Data

(60) Provisional application No. 62/371,996, filed on Aug. 8, 2016.

(51) Int. Cl.
*G01N 27/82*    (2006.01)
(52) U.S. Cl.
CPC .................... *G01N 27/82* (2013.01)
(58) Field of Classification Search
CPC ................. G01N 27/82; G01N 27/83
See application file for complete search history.

(56) References Cited

U.S. PATENT DOCUMENTS

| 2,497,855 A * | 2/1950 | Barnes ............... G01N 27/9033 |
| | | 324/217 |
| 4,602,212 A | 7/1986 | Hiroshima et al. |
| 8,447,532 B1 | 5/2013 | Goroshevskiy et al. |
| 8,542,127 B1 | 9/2013 | Goroshevskiy et al. |
| 9,651,471 B2 | 5/2017 | Davis et al. |

(Continued)

OTHER PUBLICATIONS

Anonymous: "Magnetic flux leakage—Wikipedia, the free encyclopedia", Jan. 2, 2016 (Jan. 2, 2016), XP055427962, Retrieved from the Internet: URL:https://web.archive.org/web/20160102145510/https://en.wikipedia.org/wiki/Magnetic_flux_leakage [retrieved on Nov. 22, 2017].

(Continued)

*Primary Examiner* — Daniel R Miller
(74) *Attorney, Agent, or Firm* — HoustonHogle LLP (57) ABSTRACT

The system and method involve a permanent magnetization induction process for ferromagnetic structures, carried out to the saturation point to overwhelm the intrinsic magnetic fields in the structures. The permanent magnetization to overwhelm the intrinsic magnetization eliminates the effect of intrinsic fields for subsequent measurements. The permanent magnetization along a hollow structure yields two residual magnetic field components: axial and circumferential. The circumferential component varies as a function of depth. Thus, an analysis system can analyze defects and the depth of those defects by detecting the direction of the magnetic flux leakage around the defects. This can further be performed at a distance from the structures.

17 Claims, 11 Drawing Sheets

(56) References Cited

U.S. PATENT DOCUMENTS 9,651,472 B2    5/2017   Davis et al.
2011/0037461 A1    2/2011   Braun

OTHER PUBLICATIONS

International Search Report and Written Opinion of the International Searching Authority, dated Nov. 30, 2017, from International Application No. PCT/US2017/045917, filed on Aug. 8, 2017. 17 pages.

International Preliminary Report on Patentability, dated Feb. 21, 2019, from International Application No. PCT/US2017/045917, filed on Aug. 8, 2017. 10 pages.

Boat, M. et al., "Factors that Affect the Defect Sizing Capabilities of the Magnetic Flux Leakage Technique," paper presented at the BINDT Conference, Sep. 2014. Eleven pages.

Costain, J. et al., "Capability of Modern Tank Floor Scanning with Magnetic Flux Leakage," paper presented at the 19th World Conference on Non-Destructive Testing, 2016. Eleven pages.

Feng, Q. et al., "Evolution of Triax Magnetic Flux Leakage Inspection for Mitigation of Spiral Weld Anomalies," paper presented at the 6th Pipeline Technology Conference, American Society of Mechanical Engineers, 2010. Fourteen pages.

Foerster Group, "Flux Leakage Testing: Operating Principle of the Alternating Field Leakage Flux Method," downloaded from http://www.foerstergroup.com/products/product/flux-leakage-testing/list/. Before Jun. 30, 2017. Three pages.

Göktepe, M., "Non-Destructive Crack Detection by Capturing Local Flux Leakage Field," Sensors and Actuators, A Physical No. 91, 2001, pp. 70-72. Three pages.

Hammons, T. et al., "1998 ICEM Review: Highlights of the 1998 International Conference on Electrical Machines, Istanbul, Turkey," IEEE Power Engineering Review, Feb. 1999, pp. 12-17. Seven pages.

Kandroodi, M. et al., "Detection of Natural Gas Pipeline Defects Using Magnetic Flux Leakage Measurements," paper presented at the 2013 21st Iranian Conference on Electrical Engineering, May 2011 Six pages.

Kreutzbruck, M. et al., "Adapted Gmr Array Used in Magnetic Flux Leakage Inspection," paper presented at the 18th World Conference on Nondestructive Testing, Apr. 2012. Eight pages.

Li, Y. et al., "Experiment and Simulation Study of 3D Magnetic Field Sensing for Defect Characterisation," Proceedings of the 12th Chinese Automation & Computing Society Conference in the UK, Sep. 2006. Six pages.

Li, Y. et al., "Numerical Simulation on Magnetic Flux Leakage Evaluation at High Speed," Non Destructive Testing & Evaluation International, Jul. 2006. Eleven pages.

Lunin, V. et al., "Numerical Prediction of Signal for Magnetic Flux Leakage Benchmark Task," Review of Quantitative Nondestructive Evaluation, vol. 22, 2003, pp. 1830-1837. Eight pages.

Mandache, C. et al., "A Model for Magnetic Flux Leakage Signal Predictions," Journal of Physics D: Applied Physics, vol. 36, 2003, pp. 2427-2431. Five pages.

Miller, S. et al. "Advances in Feature Identification Using Tri-Axial MFL Sensor Technology," paper presented at the Pipeline Technology Conference 2008, American Society of Mechanical Engineers. Thirteen pages.

Miller, S. "Prediction of Dent Size Using Tri-Axial Magnetic Flux Leakage Intelligent Pigs," paper presented at the NACE Conference, Mar. 2007. Nine pages.

Nipun, "Difference Between Magnetic Field and Magnetic Flux," Oct. 2015, http://pediaa.com/difference-between-magnetic-field-and-magnetic-flux/. Four pages.

Pearson, N. et al., "A Study of MFL Signals from a Spectrum of Defect Geometries," paper presented at the 18th World Conference on Nondestructive Testing, Apr. 2012. Seven pages.

Rao, B., "Magnetic Flux Leakage Technique: Basics," Journal of Non Destructive Testing and Evaluation, vol. 11, No. 3, Dec. 2012, pp. 7-17. Eleven pages.

Saha, S. et al., "Empirical Structure for Characterizing Metal Loss Defects from Radial Magnetic Flux Leakage Signal," Non Destructive Testing and Evaluation International, vol. 43, 2010, pp. 507-512. Six pages.

Shi, Y. et al., "Theory and Application of Magnetic Flux Leakage Pipeline Detection," Sensors, vol. 15, No. 12, Dec. 2015, pp. 31036-31055. Twenty-one pages.

Tang, Y. et al., "Experimental and Finite Element Analysis Study of 3D Magnetic Field Sensing for Pulsed Magnetic Flux Leakage Defect Characterisation," Insight—Non-Destructive Testing and Condition Monitoring, vol. 53, No. 9, Sep. 2011, pp. 497-506. Abstract. Six pages.

Wang, Z. et al., "A Review of Three Magnetic NDT Technologies," Journal of Magnetism and Magnetic Materials, No. 324, Feb. 2012, pp. 382-388. Eight pages.

Wilson, J. et al., "3D Magnetic Field Sensing for Magnetic Flux Leakage Defect Characterisation," Insight, vol. 48, No. 6, Jun. 2006, pp. 357-359. Three pages.

\* cited by examiner

AXIAL FIELD INDUCTION

CIRCUMFERENTIAL
FIELD INDUCTION

METHOD FOR DETERMINING DEFECT DEPTH IN FERROMAGNETIC STRUCTURES BASED ON MAGNETIC FLUX LEAKAGE DIRECTION

RELATED APPLICATIONS

This application claims the benefit under 35 USC 119(e) of U.S. Provisional Application No. 62/371,996, filed on Aug. 8, 2016, which is incorporated herein by reference in its entirety.

BACKGROUND OF THE INVENTION

Ferromagnetic materials, such as iron, nickel, steel and other materials, are used to make many structures, such as beams in buildings, pipes, parts of machinery or vehicles, and ocean vessel hulls, to list a few examples. As used herein, "ferromagnetic materials" include both ferromagnetic and ferrimagnetic materials. These materials have hysteretic properties, which allow them to retain residual magnetic fields and to become permanently magnetized. As used herein, "permanently magnetized" refers to aligning magnetic domains to create an internal residual field which remains without the presence of any external field. In many cases, these materials are subject to fatigue, corrosion and/or erosion. As used herein, corrosion means loss of material as a result of chemical reaction, most commonly oxidation. As used herein, erosion means loss of material as a result of a mechanical process, such as abrasion. For example, sand produced in oil or gas wells can abrade the inside of a pipeline carrying oil or gas from the well. Material loss due to corrosion and/or erosion is collectively referred to herein as a "defect." As used herein, the term defect also includes a crack, or a void or inclusion of foreign material, such as might occur during manufacture or later. In addition, defects can also occur due to fatigue and wear. If allowed to proceed beyond a critical point, defects may lead to catastrophic failures such as collapse or an oil spill.

Visual inspection for defects in ferromagnetic structures is typically not practical for structures that are hidden from sight. For those instances where visual inspection is practical it will find the most obvious damages not the subtle ones. Therefore, various apparatus and non-visual methods have been used in the prior art in attempts to detect defects in ferromagnetic structures and items made of ferromagnetic materials. Some of these apparatus and methods require removing thermal insulation and striping off corrosion inhibiting surface treatments to gain direct access to a surface of the ferromagnetic material. In some cases, the surface must be polished to create a pristine interface to a sensor or wave propagation from the sensor. These steps are costly, time-consuming and often compromise the thermal insulation and/or the surface treatments.

Some prior art apparatus and methods involve magnetometry in attempts to detect defects in ferromagnetic materials. For example, U.S. Pat. Nos. 8,542,127 and 8,447,532, both by Valerian Goroshevskiy, et al., disclose using the inverse magnetostrictive Villari effect. The inverse magnetostrictive Villari effect involves changes in a material's magnetic susceptibility under applied mechanical stress. If a structure suffers a defect, the structure's magnetic susceptibility when the structure material is mechanically stressed, for example when the structure is pressurized, is different than when the structure is not mechanically stressed. The Goroshevskiy patents rely on detecting this change in magnetic susceptibility as pressure within the structure changes. Thus, energy must be introduced into the structure in the form of pressurizing the inferior of the structure. Some structures remain unused, and therefore unpressurized, for periods of time during which defects may develop. Other structures, such as ship hulls or structural elements, do not lend themselves to known pressurization cycling. However, without pressurization, the Goroshevskiy apparatus and methods cannot detect these defects. Furthermore, Goroshevskiy can determine a defect's location only along the length of a structure; Goroshevskiy cannot determine the defect's location circumferentially around the pipe.

Two more recent patents, U.S. Pat. Nos. 9,651,472 and 9,651,471, disclose characterizing defects using magnetic flux leakage (MFL) from ferromagnetic pipes. These patents describe an approach in which arrays of magnetometers disposed about a surface of the ferromagnetic material to sense its magnetic field. This yields magnetic flux data that can be rendered into two-dimensional maps. A pattern matcher can then be used to identity defects.

MFL technique is an established technique. For example, see Miller, "Prediction of Dent Size using Tri-axial Magnetic Flux Leakage Intelligent Pigs", Document Id: NACE-07138, NACE International, 2007. Note that PIG is an acronym for Pipeline Inspection Gauge. Miller's review article points out use of MFL techniques that primarily collect data on-skin or near-skin from defects on ferromagnetic pipes.

Transkor Group, Inc., from Houston, Tex., and Energo-diagnostika, a Russian company, have developed methods, classified as large standoff magnetometry (LSM) for passively measuring the magnetic flux leakage of defects at large standoff distances.

SUMMARY OF THE INVENTION

This invention concerns a method and a system to create and use pre-magnetized ferromagnetic structures, where magnetic field direction rotates with depth, and analyze the nature of defects in the structures. These structures may be accessible or not directly accessible. Examples include analyzing the magnitude and direction of MFL from magnetized pipes or other man-made objects or equipment that are buried underground, or in buildings, or in machinery or vehicles.

The system and method involve a permanent induced magnetization process of ferromagnetic structures, carried out to the saturation point to overwhelm the intrinsic magnetic fields in the structures. The intrinsic fields are due to the structures' internal fields induced by earth's magnetic field and parasitic fields caused as a byproduct of manufacturing of the structures. Parasitic components of the intrinsic field may occur during manufacturing because individual magnetic dipoles in iron, for example, may partially align with the Earth's magnetic field after cooling below the Curie temperature when cast or hot-rolled in the foundry. The permanent magnetization to overwhelm the intrinsic magnetization basically eliminates the effect of intrinsic fields for subsequent measurements. The permanent magnetization along a structure is induced as two residual magnetic field directions: typically axial or longitudinal and circumferential or lateral, for example.

In an axial magnetization process, the magnetic field is induced by surrounding the structure with Helmholtz-type or solenoidal coils and passing current through the coils. The axial magnetic field thus created is constant along the structure and its cross-section.

In a circumferential magnetization process, the magnetic field is induced by passing current of uniform density (amperes per square meter) along the structure for cylindrical geometries. The circumferential magnetic field, along the tangent to the circumference, varies linearly from being the highest on the outer edge of the structure to zero in the interior edge of the structure.

If the axial and circumferential magnetization processes are carried out simultaneously on a hollow cylindrical structure, the residual field on the skin of the structure will be about 45 degrees off the cylindrical axis. The internal residual magnetization will be purely axial, 0 degree off-axis. Thus, the field will vary from 45 degrees off-axis on surface to 0 degree off-axis (purely axial) with depth.

In another method, which is the preferred method, circumferential magnetization may be carried out after first performing axial magnetization, which will result in erasing the axial field on surface of the skin but will have zero effect inside the structure. Thus, the field will vary from 90 degrees off-axis on surface skin (purely circumferential) to 0 degree off-axis (purely axial) with depth.

There are other ways of generating a magnetic field that rotates with depth. For example, generating high frequency alternating II-fields near the structure will induce a permanent magnetization with a depth dependency within the structure due to the skin effect.

One or more magnetometers, such as magnetometer arrays (of preferably 3-axis magnetometers), located on or near the surface of structures or at large or small standoff distances, measure magnetic flux emanating and leaking from the structures at their surface. In defect-free structures, the circumferential and axial fields will not leak from the ferromagnetic structure. As a defect grows and deepens, the direction of the magnetic flux leakage emanating from the structure, θ (angle along the axis), will change in proportion to the defect depth. In other words, the nature of the defect (e.g., depth, cross-section of the defect and volume) will lead to varying measurement direction/pattern of the magnetic flux.

In general, according to one aspect, the invention features a method for analyzing ferromagnetic structures. This method comprises permanently magnetizing the structures to create a residual magnetic field that varies in direction as a function of depth in structures. Then, the direction of the magnetic flux leakage is detected. The direction of the magnetic flux leakage is analyzed to identify defect dimensions in the structure.

In the current embodiment, permanently magnetizing structures comprises magnetizing the structures in a predetermined direction. Then, they are permanently magnetized to create a magnetic field that varies as a function of depth in the structures.

In a typical case, a structure is first magnetized with a uniform magnetic field in the axial or longitudinal direction. Second, the structure is permanently magnetized in the circumferential direction with strength that varies with depth. The circumferential field completely erases the axial field on the top of the structure, generated in the first axial magnetization step. But inside the structure the axial field generated in the first step remains intact. After the two magnetization steps are complete, the net residual magnetic field, vector sum of axial and circumferential components, will vary in strength and direction from top of the surface of the structure to inside the structure.

When analyzing the flux leakage, to identify defects, both the magnitude of the leakage and its direction are detected. The direction of the detected leakage is then related to defects and specifically the depth of those defects in the structure at small or large standoffs.

In general, according to another aspect, the invention also covers a method for permanently magnetizing ferromagnetic structures to facilitate analysis. This method includes permanently magnetizing structures with a first magnetic field in a predetermined direction. Then, the structures are permanently magnetized with a second magnetic field that varies as a function of depth in the structures. In this way, the structures can be later analyzed for defects and the depth of those defects can be determined based upon the direction of the magnetic flux leakage measured at small or large standoffs.

The method also covers using permanently magnetized ferromagnetic structures to facilitate analysis without regard to how the magnetization is induced, but with the requirement that magnetization vary with depth, or possibly another dimension. The magnetization can also be performed in-situ. In this way, the structures can be later analyzed for defects and the depth of those defects can be determined based upon the direction of the magnetic flux leakage measured at small or large standoffs.

In general according to another aspect, the invention features a system for analyzing ferromagnetic structures. This system comprises a magnetization system that permanently magnetizes structures to create a permanent magnetic field that varies as a function of depth in the structures. An analysis system then detects the direction of the magnetic flux leakage from the structures and analyzes the flux leakage to identify defects in the structures.

The system can also comprise using permanently magnetized structures regardless of how the magnetization is induced as long as the permanent magnetic field varies as a function of depth in the structures. The magnetization can also be performed in-situ. An analysis system then detects the direction of the magnetic flux leakage from the structures and analyzes the flux leakage to identify defects in the structures.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

In general, a system and associated methodology are disclosed for detecting ferromagnetic structural characteristics, such as defects, by analyzing MFL data from arrays of 3-axis magnetometers, either affixed to the skin of pre-magnetized structures or located at a standoff distance from the pre-magnetized structures. The system and methodology can also characterize the nature (e.g., depth and volume) of defects, which is crucial for judging the severity of defects so that potential catastrophic failures can be avoided.

Figure 1:
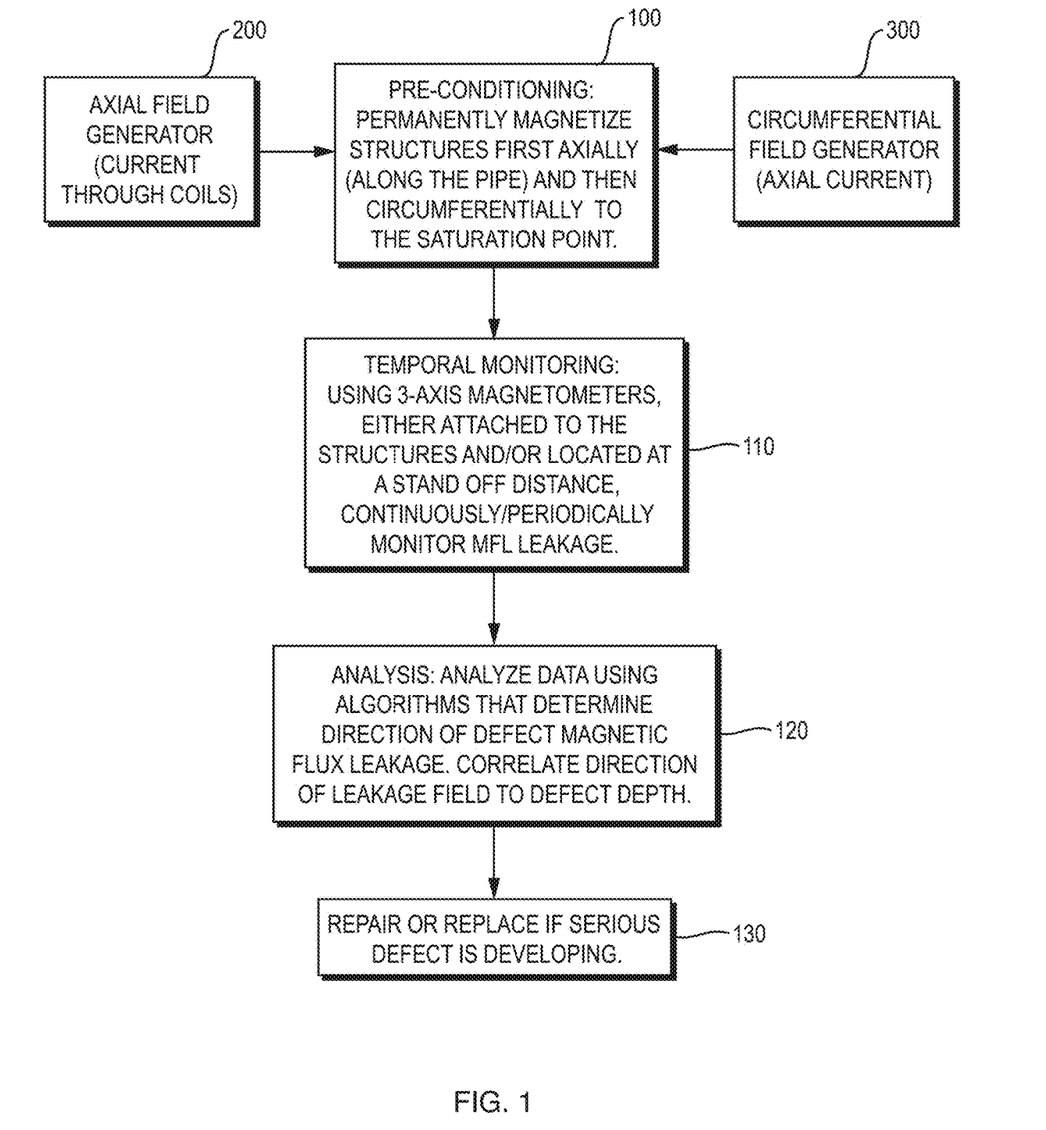
FIG. 1 is a flowchart showing pre-conditioning ferromagnetic structures and eventually characterizing defects using MFL data, according to the invention.

FIG. 1 shows the pre-conditioning of ferromagnetic structures and characterization of defects using MFL data, according to the principles of the present invention.

In step 100, the ferromagnetic structures are pre-conditioned by strongly and permanently magnetizing them. This pre-conditioning can occur before they are installed, for example, as sections of a pipeline, or it may be used in-situ on previously installed structures. Of course, this can be applied to other structures. For example, in other examples the structures are part of a building, factory, or other facility or machinery, such as a wind turbine. In still other examples, the structure could be part of a vessel such as the hull of a ship or mining machine.

This pre-magnetization of the structures ensures that once a defect occurs, the magnetic field of the structures will be perturbed and the perturbation will manifest itself as MFL from the detect. Strong pre-magnetization ensures that the structures are standardized to have a well-defined magnetization and its strength and direction overwhelms any pre-existing weak intrinsic magnetic fields in the ferromagnetic structures.

The structures are first strongly magnetized axially using an axial magnetization system 200. More generally, however, this magnetization could be performed in a number of directions. The critical characteristic is that the structures are given a uniform magnetization in a known direction.

The structures are then circumferentially magnetized using a second, e.g., circumferential) magnetization system 300. More generally, however, the critical characteristic is that the direction is different than the first magnetization, and its strength varies with depth. The net result is that the direction of the magnetic field now has a depth-dependency.

In step 110, the structures are continuously or periodically monitored for MFL leaking out of nascent defects. The monitoring of axial and circumferential MFL is carried out by a magnetometer or an array of magnetometers collecting data at different points along the structures, such as pipelines. The magnetometers can be in contact with the structures or at standoff distances.

In step 120, the direction of the MFL is extracted from the measurement data and used to determine detect depth. Once defect depth is determined from the MFL direction, classical methods can be used to disambiguate defect depth and volume in the far field, and then defect area can be estimated. Typically, this process is performed by a controller or by a workstation that is provided with the data collected from the magnetometer or array of magnetometers.

If it is established that defects are a danger to surroundings, in step 130 corrective action is undertaken.

Figure 2A:
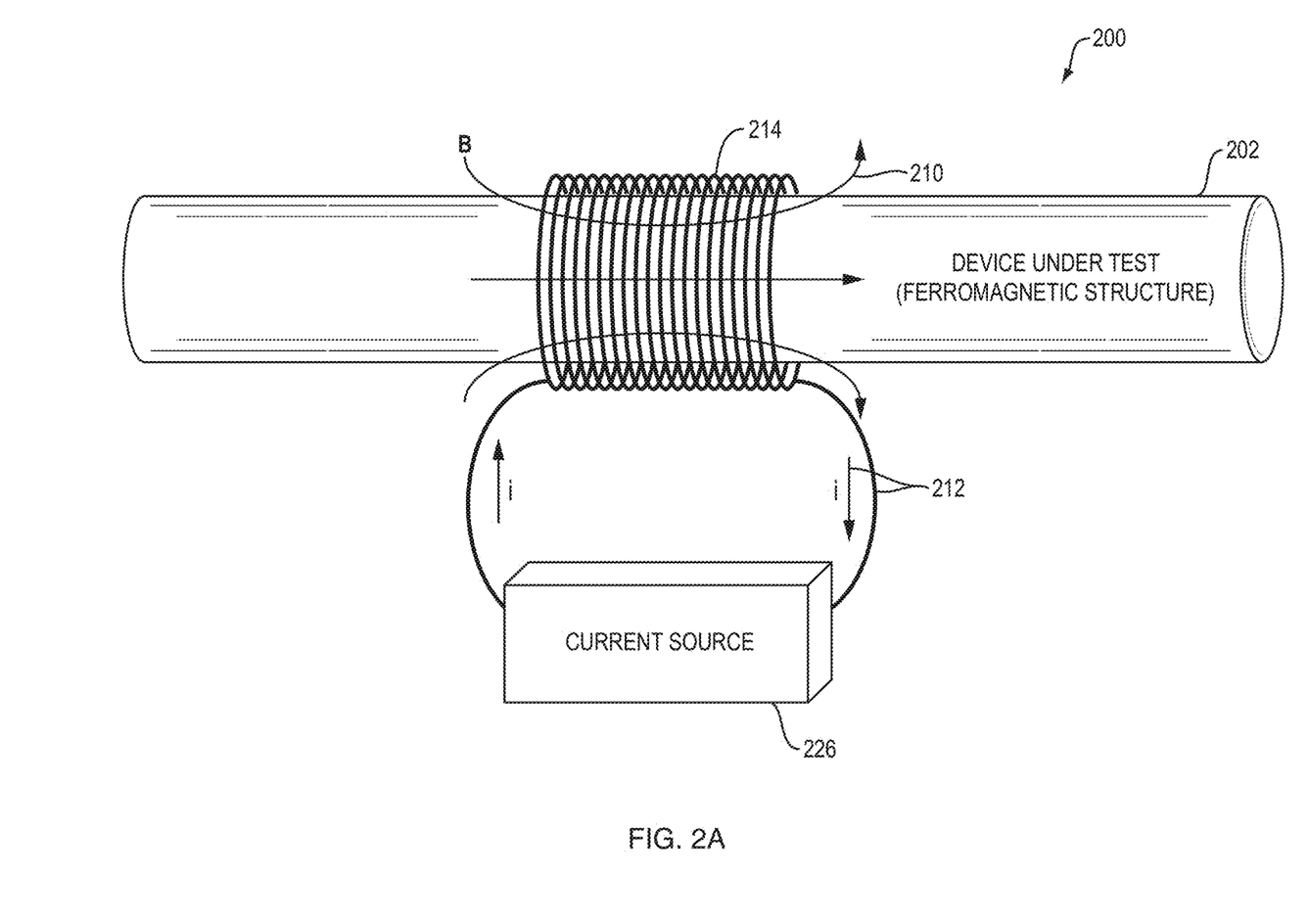
FIG. 2A is a schematic perspective view showing an axial magnetization system for axially magnetizing a structure, where. B and i denote magnetic field and current, respectively.

FIG. 2A shows the axial magnetization system 200 for generating the axial field (B) 210. The structure 202 is wrapped with Helmholtz or solenoidal coils 214 of the axial magnetization system 200. Turning on the current source 226 passes current through the coil wires 214, generating an axial magnetic H-field along the pipe 202 as shown. This H-field should be sufficiently strong to saturate the ferromagnetic material.

Following Ampere's Law, the magnetic field is perpendicular to flow of current (I) 212. Here the axial field is generated by circumferentially passing the current.

Figure 2B:
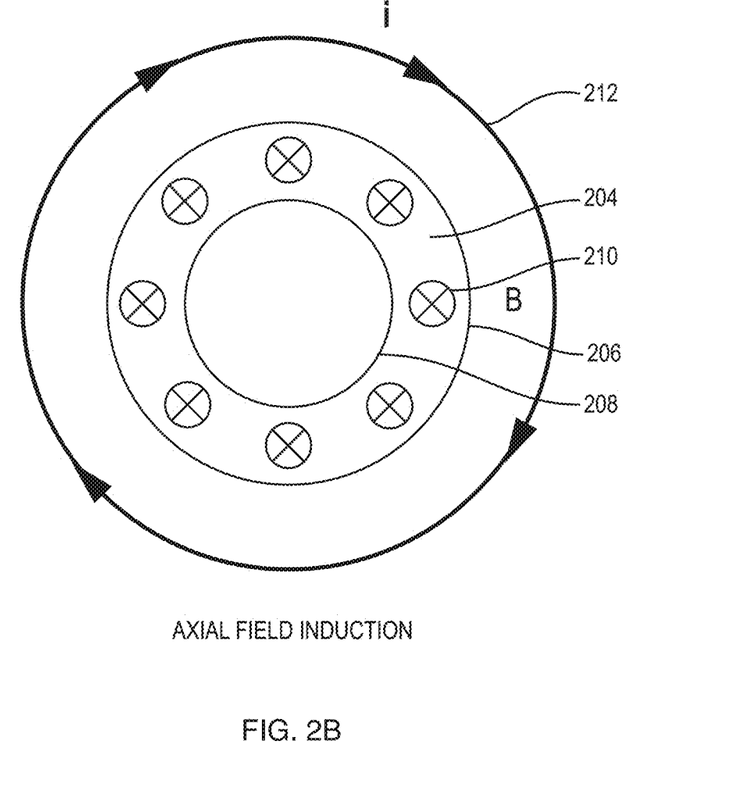
FIG. 2B is a schematic cross-sectional view of the structure showing the axial residual magnetic field as viewed from the left end of the structure in FIG. 2A.

FIG. 2B shows the cross-section of a structure 202 as viewed from its tail end (left side). The annular region 204 has an outer radius 206 and an inner radius 208. The symbols ⊗ 210 denote that the axial B field is pointing into the paper.

Figure 3A:
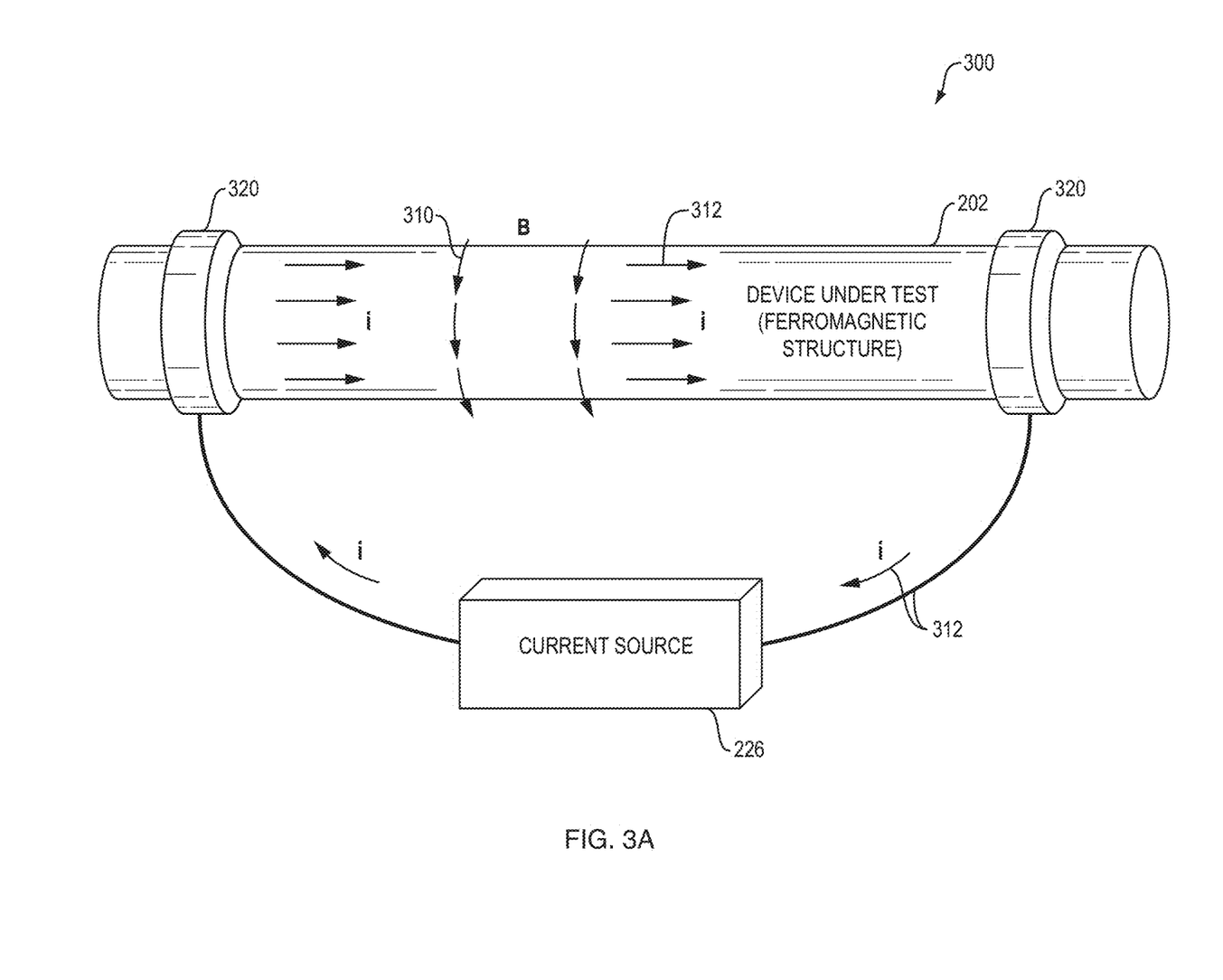
FIG. 3A is a schematic perspective view showing a circumferential magnetization system for circumferentially magnetizing the structure, where B and i denote magnetic field and current, respectively.

FIG. 3A shows the circumferential magnetization system 300 for generating the circumferential field (B) 310 by axially passing current 312 through the structure 202.

The brackets 320 are installed at each end of the structure and connected to a current source 226. Turning on the axial current, generates the circumferential field 310. The strength of the circumferential field at the outer edge 206 of the structure should be of sufficient strength to saturate the ferromagnetic material out of which the structure is made. This overwhelms the field generated by the axial magnetization step at the outer surface, while leaving the axial magnetization intact at the inner surface.

Figure 3B:
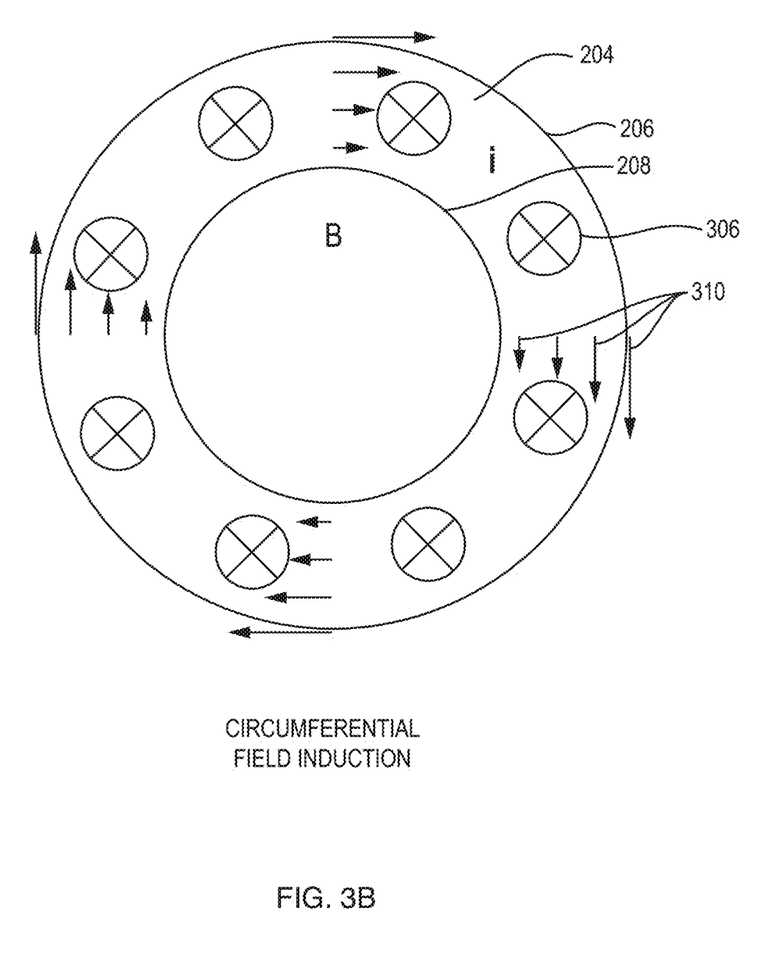
FIG. 3B is a schematic cross-sectional view of the structure showing the circumferential magnetic field as viewed from the left end of the structure in FIG. 3A.

FIG. 3B shows the cross-section annular region 204 of the structure 202 as viewed from its tail end (left side). Because of Ampere's Law, the circumferential field falls off being the strongest at the outer surface of the annular region to completely vanishing to zero at the inner radius 208. The reason for this is that the enclosed current decreases from maximum to zero as the enclosing radius varies from 206 (outer edge) to 208 (inner edge). The symbols ⊗ 306 denote that the current is flowing into the paper.

The net residual field will be a vector sum of axial and circumferential components and will rotate from being almost completely axial (x in FIG. 4) at the inner radius to being almost completely circumferential (y in FIG. 4) at the outer radius edge of the structure.

There are other ways of generating a magnetic field that rotates with depth. For example, inducing generating high frequency alternating currents H-fields near in the structure will push induce the current to flow a permanent magnetization with a depth dependency within the structure due to the skin effect. Thus, the residual field can be manipulated to rotate with depth.

Figure 4:
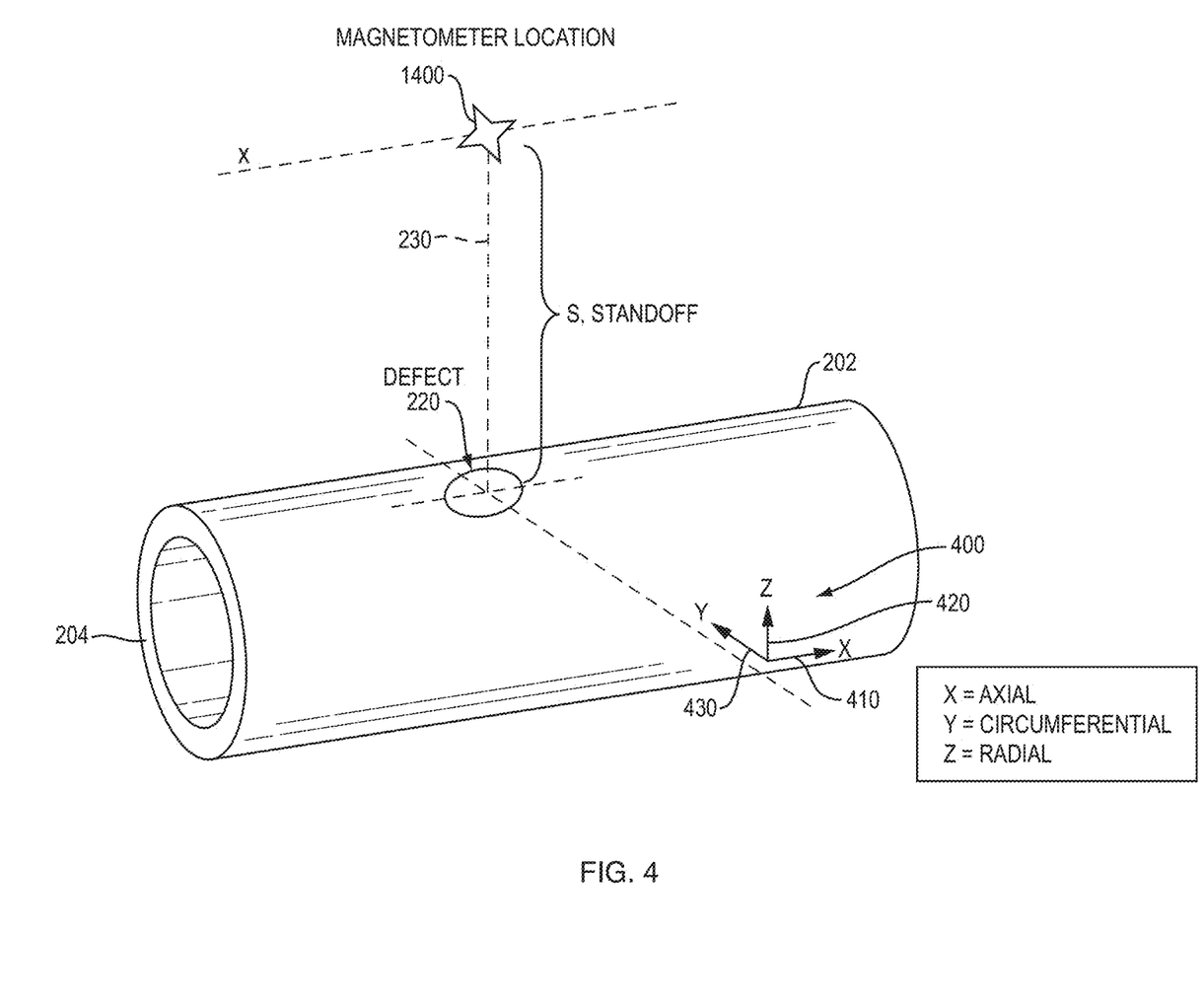
FIG. 4 is a schematic perspective view of the geometry to measure MFL from a structure, along with the coordinate system.

FIG. 4 shows the geometry of the measurement setup and an orthogonal coordinate system 400. The geometry is for a general standoff (S) 230 where the standoff is the distance of the detector (magnetometer array) from the defect 220 on the structure. If S is zero, the measurement will convert to on-skin measurement. The orthogonal coordinate system is defined such that x-axis 410 is along the length of the structure. The z-axis 420, towards the detector array 1400, is termed the radial axis. They-axis is denoted as 430, and is termed the circumferential axis.

Figure 5:
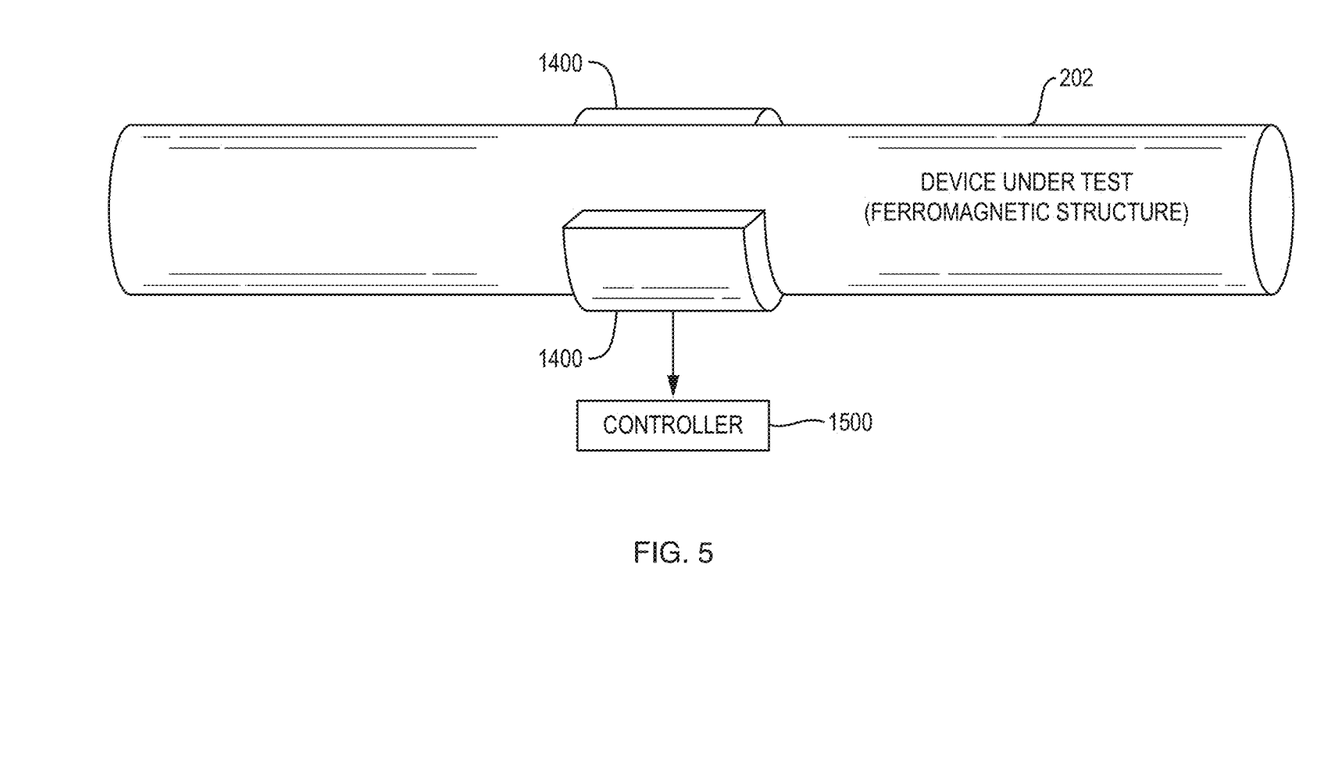
FIG. 5 is a schematic perspective view of a magnetometer array almost encircling the skin of a structure to make MFL measurements. Although pictured on the skin in this figure, this method of determining the defect depth by measuring flux direction will work at far-field standoffs as well.

FIG. 5 is a schematic of an embodiment of a magnetometer array 1400 setup to carry out an on-skin measurement of MFL from a structure 202. The magnetometer array communicates with controller 1500.

In general, the controller 1500 analyzes both the magnitude of magnetic flux leakage and the direction of the leakage from each of the 3-axis magnetometers of the array 1400 to assess the structure and defects in the structure. The controller 1500 analyzes the detected MFL as a function of position on the structure 202 and potentially over time and determines characteristics of the structure such as defects.

Figure 6A:
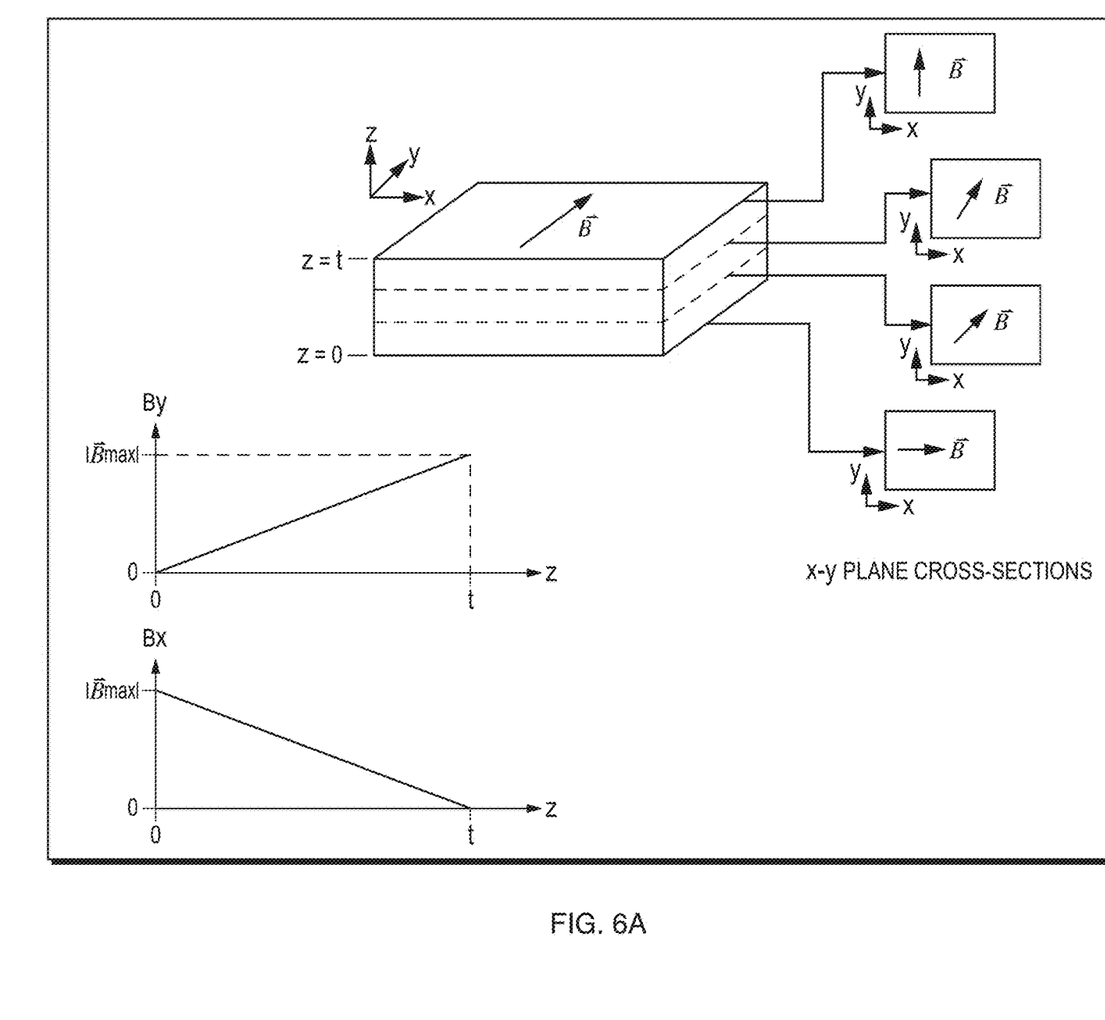
FIG. 6A is an idealized schematic perspective view showing the rotation of the residual magnetic field direction as a function of depth in a pre-conditioned structure wall.

FIG. 6A shows an idealized schematic of the direction of the residual field inside a pre-conditioned structure. If a defect were to form in the structure depicted in FIG. 6A, the direction of MFL would correlate to the depth and origin of the defect. For example, from a superficial defect on top surface, z=t, of the structure, MFL would leak out in the y-direction. If the defect proceeds to get deeper towards bottom, z=0, the direction of leakage would rotate continuously towards the x-direction.

If on the other hand a defect started from the bottom, z=0, the opposite would occur. The flux would start leaking in they-direction and rotate towards x-axis as the defect grew deeper.

As a result, the controller 1500 (FIG. 5), equipped with analysis software/hardware, can perform depth assessment of any defects from far-field distances (i.e., distances much larger than the defect) by tracking the direction of the magnetic flux at each point along the structure. In other words, two defects of same volume but of different depths would yield MFL oriented differently. Traditionally, non-directional MFL only yields volume of defects whereas the technique here would also yield their depths.

Figure 6B:
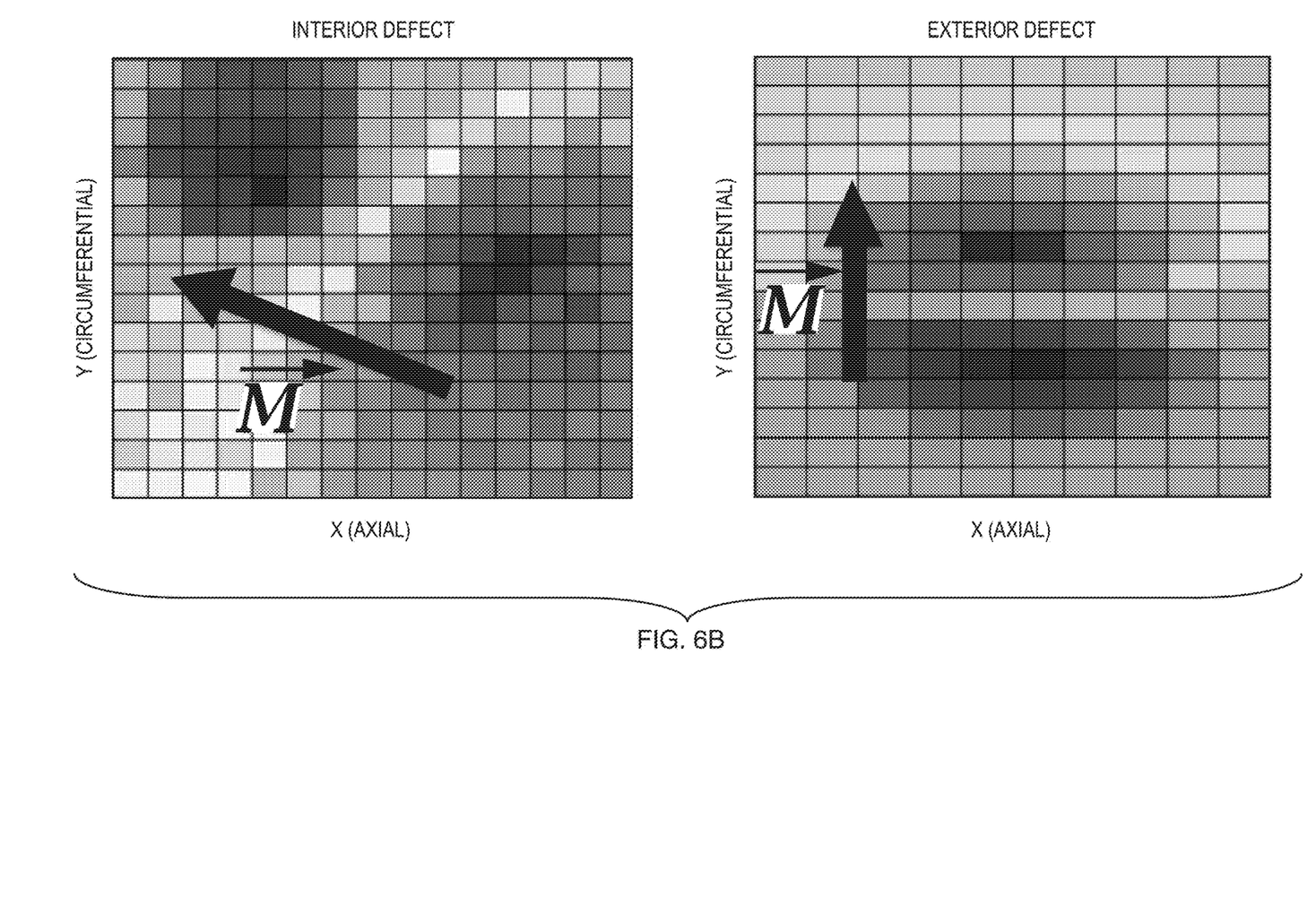
FIG. 6B is a contour plot of measurement data showing the radial component of the MFL (B) for a shallow interior and exterior defect as one views the structure in a radial direction, looking down. Note that the pattern suggests the direction of the MFL for these two defects are rotated with respect to each other.

FIG. 6B is actual measurement data of MFL from an interior and an exterior defect which are. The leakage from interior defect is mostly axial whereas the leakage from exterior defect is mostly circumferential in direction.

Figure 7:
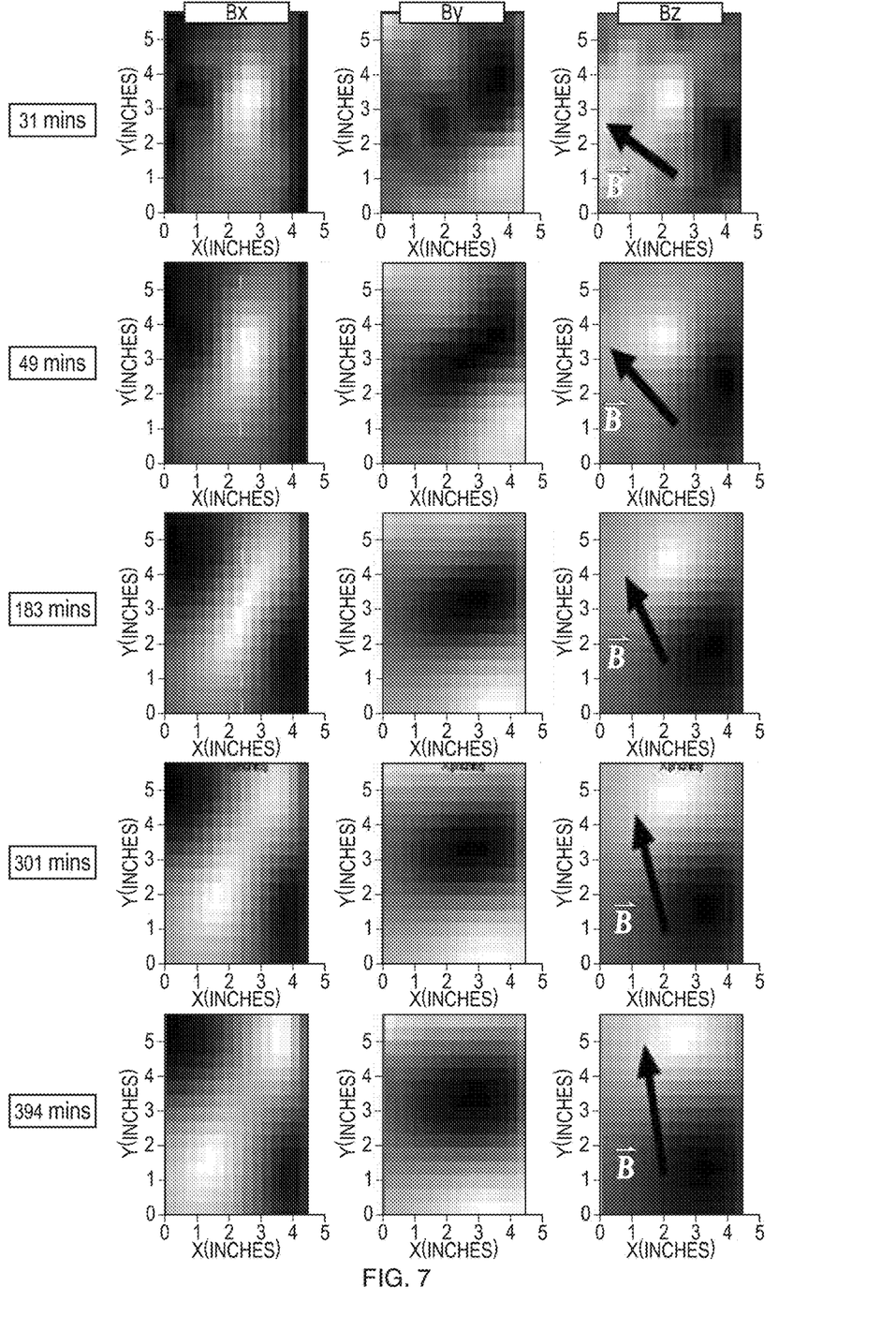
FIG. 7 shows contour plots of measured data for all three MFL components as a defect develops in time, t. The values plotted are on the xy-plane for t=31, 49, 183, 321 and 394 minutes into the etching process which creates the defect. The direction of the magnetic flux leakage (B) is identified in the $B_z$ contour plots (i.e., surface plots projected on the xy-plane).

FIG. 7 shows MFL, data collected from an internal defect as it progresses. The defect is caused by etching the structure chemically. The depth of defect increases as time increases. The values plotted are in the form of contour plots (bottom row) of $B_x$, $B_y$ and $B_z$, respectively, on the xy-plane at t=31, 49, 183, 301 and 394 minutes of etching. The general observations are that radial $B_z$ "lobes" rotate, axial $B_x$ goes from even function to quadrupole and $B_y$ goes from quadrupole to even function as the etch gets deeper with time. This is consistent with what one would expect to see as the MFL leakage direction rotates with depth.

Clearly, the experimental results indicate that characteristics of defects are strong determinants of the observed MFL magnitude and direction. Specifically, the direction of the MFL is a strong determinant of the depth of the defect. Indeed, observed MFL can be parameterized in a functional relationship that relates measured MFL to parameters standoff distance, volume and depth of defect, and variables x, y and z. of the coordinate system.

Figure 8:
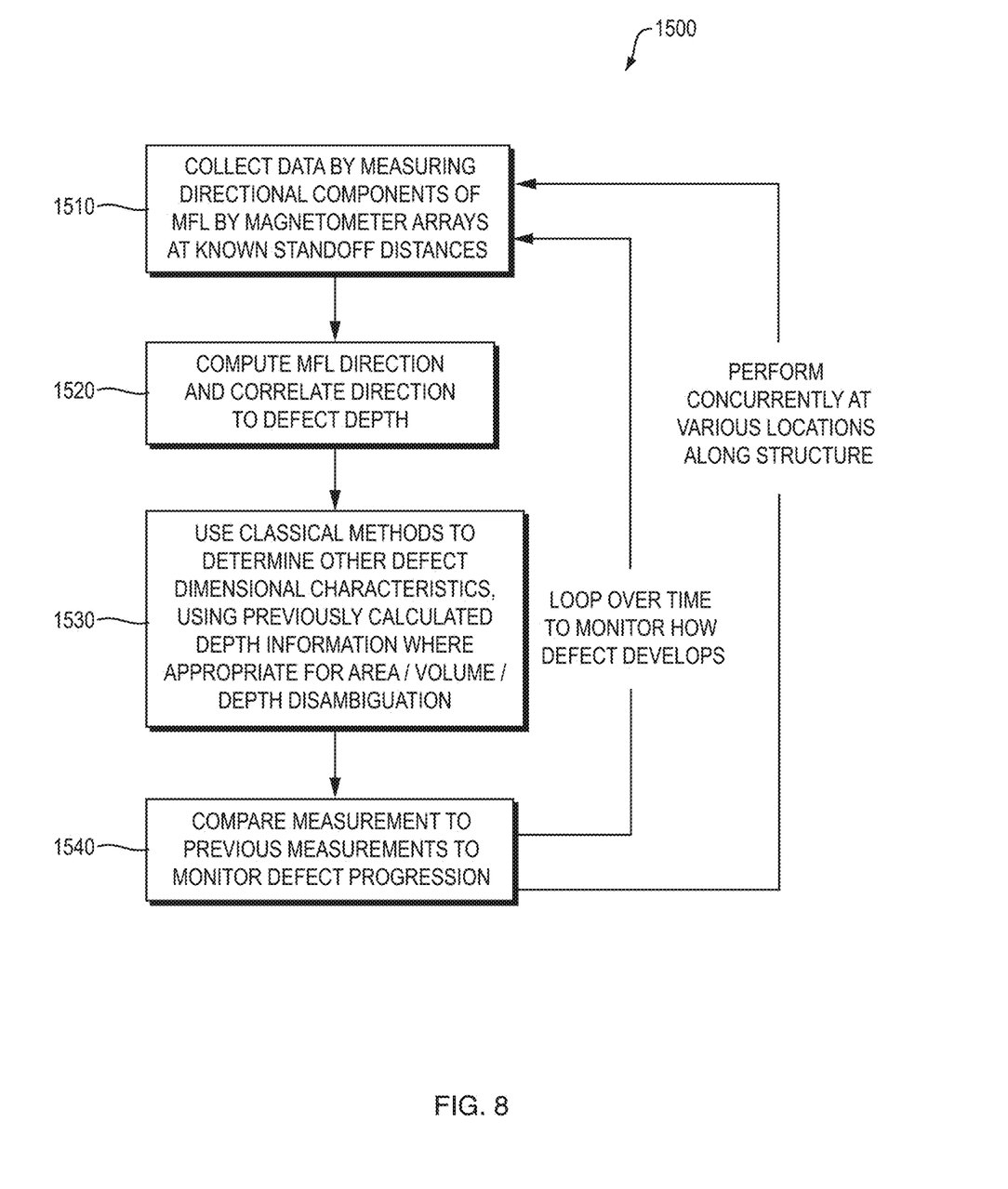
FIG. 8 is a flow diagram showing the operation of the controller of the MFL, system.

FIG. 8 is a flow diagram illustrating the operation of the controller 1500 or other computer system that has access to the magnetic MFL magnitude and direction collected by the three axis magnetometer array 1400 over the extent of the structure.

In more detail, the controller 1500 collects magnetometer raw data in step 1510. The data will be spatial maps of the magnitude of MFL along the three directions. The maps should preferably cover the entire extent of the structure 202.

The data are then used to compute the direction of the MFL signature in step 1520. MFL direction is then used to compute defect depth.

Then in step 1530 classical MFL techniques are used to compute volume in far-field or area in near field. This information is augmented with depth information determined in 1520 to accurately size defect. This process is carried out at various time intervals to monitor progress of defects in step 1540. Finally, this process must be carried out concurrently at various locations along the structure for complete assessment of potential failure.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for analyzing ferromagnetic structures, comprising:
   permanently magnetizing the structures to create a permanent magnetic field that varies as a function of depth in the structures by first placing the structures in a Helmholtz coil and passing an electric current through the structures;
   detecting direction of magnetic flux leakage; and
   analyzing the flux leakage to identify defects in the structures.

2. A method as claimed in claim 1, further comprising permanently magnetizing the structures with a first magnetic field in a direction.

3. A method as claimed in claim 2, wherein the magnetic structures are first permanently magnetized with the first magnetic field, which is generated by the Helmholtz coil, in the direction and then permanently magnetized to create a permanent magnetic field that varies as a function of depth in the structures with the electric current.

4. A method as claimed in claim 1, wherein permanently magnetizing the structures to create the permanent magnetic field that varies as with depth comprises magnetizing the structures in a circumferential direction.

5. A method as claimed in claim 1, wherein permanently magnetizing the structures in the direction comprises magnetizing the structures in an axial direction.

6. A method as claimed in claim 1, wherein analyzing the flux leakage to identify defects in the structures comprises detecting flux leakage and direction of the leakage from the structures.

7. A method as claimed in claim 1, further comprising relating flux leakage and the direction of the leakage from the structures to defects and depth of the defects in the structures.

8. A method as claimed in claim 1, wherein the structures are pipeline sections.

9. A method for permanently magnetizing ferromagnetic structures to facilitate analysis, comprising:
   permanently magnetizing the structures with a first magnetic field in a direction by placing the structures in a Helmholtz coil; and then
   permanently magnetizing the structures with a second magnetic field that varies as a function of depth in the structures by passing an electric current through the structures.

10. A method as claimed in claim 9, wherein the first magnetic field is a uniform magnetic field over an extent of the structure.

11. A method as claimed in claim 9, wherein the structures are pipeline sections.

12. A system for analyzing ferromagnetic structures, comprising:
   a structural magnetization system that permanently magnetizes the structures to create a permanent magnetic field that varies as a function of depth in the structures, including a Helmholtz coil for magnetizing the structures in a predetermined direction, and an electric current source that generates a depth dependent magnetization in the structures by passing an electric current through the structures; and
   an analysis system that detects direction of magnetic flux leakage from the structures and analyzes the flux leakage to identify defects in the structures.

13. A system as claimed in claim 12, wherein the analysis system detects flux leakage and direction of the leakage.

14. A system as claimed in claim 13, wherein the analysis system relates flux leakage and the direction to defects and depth of the defects in the structure.

15. A system as claimed in claim 12, wherein the structures are pipeline sections.

16. A system for permanently magnetizing ferromagnetic structures to facilitate analysis, comprising:
   a Helmholtz coil for permanently magnetizing the structures with a first magnetic field in a predetermined direction; and
   an electric current source for permanently magnetizing the structures with a magnetic field that varies as a function of depth in the structures by passing electric current through the structures.

17. A system as claimed in claim 16, wherein the structures are pipeline sections.

* * * * *